United States Patent
Coulston et al.

(10) Patent No.: US 7,381,187 B2
(45) Date of Patent: *Jun. 3, 2008

(54) BLOOD PRESSURE MONITORING SYSTEM AND METHOD OF HAVING AN EXTENDED OPTICAL RANGE

(75) Inventors: George W. Coulston, Pittsburgh, PA (US); Thomas A. Micka, West Grove, PA (US)

(73) Assignee: Textronics, Inc., Wilmington, DE (US)

( * ) Notice: Subject to any disclaimer, the term of this patent is extended or adjusted under 35 U.S.C. 154(b) by 546 days.

This patent is subject to a terminal disclaimer.

(21) Appl. No.: 10/937,121

(22) Filed: Sep. 9, 2004

(65) Prior Publication Data

US 2005/0277837 A1 Dec. 15, 2005

Related U.S. Application Data

(60) Provisional application No. 60/526,187, filed on Dec. 2, 2003, provisional application No. 60/256,429, filed on Dec. 2, 2003, provisional application No. 60/526,188, filed on Dec. 2, 2003, provisional application No. 60/502,760, filed on Sep. 12, 2003, provisional application No. 06/502,751, filed on Sep. 12, 2003, provisional application No. 60/502,750, filed on Sep. 12, 2003.

(51) Int. Cl.
*A61B 5/02* (2006.01)

(52) U.S. Cl. .......................... 600/490; 606/202

(58) Field of Classification Search ................ 600/490, 600/485, 499; 73/1.01, 1.16, 1.34, 1.79, 73/1.81; 356/432, 445; 606/202
See application file for complete search history.

(56) References Cited

U.S. PATENT DOCUMENTS

| | | | |
|---|---|---|---|
| 4,909,260 | A | 3/1990 | Salem et al. |
| 4,920,969 | A | 5/1990 | Suzuki et al. |
| 5,577,510 | A | 11/1996 | Chittum et al. |
| 5,820,567 | A | 10/1998 | Mackie |

(Continued)

FOREIGN PATENT DOCUMENTS

WO 97/14357 4/1997

OTHER PUBLICATIONS

Salutron Technology Evaluation Data Summary from www.Salutron.com.

*Primary Examiner*—Charles A. Marmor, II
*Assistant Examiner*—Anita Saidi
(74) *Attorney, Agent, or Firm*—Connolly Bove Lodge & Hutz LLP

(57) ABSTRACT

A system and method for monitoring blood pressure of a wearer has an inflatable arm cuff that is selectably inflatable to differing air pressures that incorporates a fabric having both a light transmission property and a light reflection property when the fabric is illuminated with light having wavelength(s) in the range from about 400 to about 2200 nanometers. A radiation source and a detector are attached to the fabric in relative positions such that the reception of incident radiation by the detector is directly affected by a change in the amount of light transmitted through the fabric relative to the amount of light reflected by the fabric as the fabric stretches in response to motion in the wearer's body due to changes in the flow of blood through an artery disposed beneath the fabric occurring in consonance with variations in the air pressure within the inflatable cuff.

10 Claims, 6 Drawing Sheets

U.S. PATENT DOCUMENTS

| | | | |
|---|---|---|---|
| 5,840,037 A * | 11/1998 | Tochikubo et al. | 600/499 |
| 6,168,567 B1 * | 1/2001 | Pickering et al. | 600/490 |
| 6,224,558 B1 * | 5/2001 | Clemmons | 600/490 |
| 6,322,516 B1 * | 11/2001 | Masuda et al. | 600/493 |
| 6,341,504 B1 | 1/2002 | Istook | |
| 6,360,615 B1 | 3/2002 | Smela | |
| 6,458,085 B1 | 10/2002 | Wu et al. | |
| 6,511,435 B1 | 1/2003 | Bluth et al. | |
| 6,842,722 B2 * | 1/2005 | David | 702/189 |
| 2003/0095263 A1 * | 5/2003 | Varshneya et al. | 356/477 |
| 2005/0106977 A1 * | 5/2005 | Coulston | 442/301 |
| 2005/0118914 A1 * | 6/2005 | Kuo et al. | 442/301 |
| 2007/0042179 A1 * | 2/2007 | Karayianni et al. | 428/375 |

\* cited by examiner

BLOOD PRESSURE MONITORING SYSTEM AND METHOD OF HAVING AN EXTENDED OPTICAL RANGE

CROSS-REFERENCE TO RELATED APPLICATIONS

Subject matter disclosed herein is disclosed in the following co-pending applications:

System for Monitoring Motion of a Member, U.S. Application No. 60/502,760; (LP-5345USPRV), filed Sep. 12, 2003 in the name of Chia Kuo and George W. Coulston.

Blood Pressure Monitoring System and Method, U.S. Application No. 60/502,751; (LP-5347USPRV), filed Sep. 12, 2003 in the names of George W. Coulston and Thomas A. Micka.

Reflective System for Monitoring Motion of a Member, U.S. Application No. 60/502,750; (LP-5346US PRV), filed Sep. 12, 2003 in the name of George W. Coulston;

Blood Pressure Monitoring System and Method Having Extended Optical Range, U.S. Application No. 60/526,187; (LP-5622USPRV), filed Dec. 2, 2003 in the names of George W. Coulston and Thomas A. Micka.

Extended Optical Range Reflective System for Monitoring Motion of a Member, U.S. Application No. 60/526,429; (LP-5621 USPRV), filed Dec. 2, 2003 in the name of George W. Coulston.

Extended Optical Range System for Monitoring Motion of a Member, U.S. Application No. 60/526,188; (LP-5620USPRV), filed Dec. 2, 2003 in the name of Chia Kuo and George W. Coulston.

BACKGROUND OF THE INVENTION

1. Field of the Invention

This invention relates to a system and a method for monitoring blood pressure using a fabric having predetermined optical properties that respond to the motion(s) generated by geometric changes in a body due to the conduction of blood through an artery located beneath the fabric.

2. Description of the Prior Art

The "pulse" of the heart is associated with pressure pulses known to exist in the arteries carrying blood throughout the body. The periodic pumping of the heart produces these pressure pulses, which in turn flex the artery walls in rhythm with the pumping of the heart. The maximum, or peak, pressure exerted against the arterial wall occurs during the systole phase of the beat and is termed "systolic pressure". The lowest, or baseline, pressure (known as the "diastolic pressure") occurs during the diastole phase of the beat.

As the heart beats the pressure in the arteries fluctuates (higher during the systole phase and lower during the diastole phase of each beat), and is best described by the values for the systolic and diastolic pressures. Typical practice is to express blood pressure as a ratio of the maximum and minimum values.

The generally known method to determine these two blood pressure extremes is the auscultatory method. In this method a pressure cuff is applied to a person's upper arm. This cuff includes a bladder capable of holding air at a predetermined known pressure. The cuff bladder is inflated to a pressure above the highest expected pressure to be measured, i.e., above the systolic pressure. When inflated at this highest pressure, the cuff prevents the flow of blood in the brachial artery of the arm underlying the pressure cuff. The bladder is equipped with a valve, which allows the pressure to be reduced in a controlled way.

As air is released from the bladder, blood flow in the brachial artery is re-established. The inflow of blood through the artery is accompanied by pulsing sounds known as the Korotkoff sounds. These sounds are detected using a stethoscope at a point on the brachial artery just below the pressure cuff. The falling pressure in the cuff bladder is observed while air is released.

The Korotkoff sounds are divided in five phases based on loudness and certain qualitative features. The five phases of the Korotkoff sounds are also identified with certain pressure regimes, as normal arterial blood flow is being re-established. The first phase of the Korotkoff sounds (Phase 1) is heard at about 120 millimeters of mercury (mm Hg) characterized by a sharp "thud"; this is the systolic (maximum) blood pressure. Phase 2 is identified with a pressure of about 110 mm Hg and is heard as a swishing or blowing sound. Phase 3 is identified with a pressure of about 100 mm Hg and is described as a thud that is softer than that of Phase 1. At a pressure of about 90 mm Hg the first diastolic pressure is detected, called the Phase 4 Korotkoff sound, and heard as a softer blowing sound which disappears. Phase 5 is identified with about 80 mm Hg, and is called the second diastolic pressure. This last phase is silent, meaning that a laminar blood flow has been again established. Phase 5 may be absent in some human subjects. For this reason, the first diastolic pressure of Phase 4 is recorded as the lowest pressure in the artery.

An automated auscultatory apparatus relies on detecting sound levels and complex processing of these sounds into electronic signals, which are correlated with the phases of the Korotkoff sounds. Representative of an automated arrangement that uses an auscultatory method is the measurement system disclosed in U.S. Pat. No. 6,511,435 (Bluth et al.)

The re-establishment of blood flow in an occluded artery is also accompanied by a relatively significant flexure of the arterial wall. The flexure diminishes as the artery widens with the decrease in cuff pressure. In an alternative form of blood pressure measuring apparatus, known as an oscillatory measurement system, the mechanical vibrations accompanying arterial wall flexure are transformed into sound as they enter the inflated bladder of the cuff. This sound is detectable using a microphone located in the bladder. U.S. Pat. No. 6,458,085 (Wu et al.) discloses an oscillatory blood pressure measurement arrangement. An oscillatory blood pressure measurement arrangement is also disclosed in the above-mentioned U.S. Pat. No. 6,511,435 (Bluth et al.).

One drawback of oscillatory measuring apparatus is the reliance upon a cuff bladder modified to contain a microphone and associated connections to an external signal processor. Using a microphone to detect changes in sound pressure level and recognizing a pattern from the waveform so generated is difficult.

SUMMARY OF THE INVENTION

The present invention is directed to a system and method for monitoring blood pressure by detecting motion due to geometric changes in the wearer's body.

The present invention is usable with an inflatable arm cuff that is selectably inflatable to differing air pressures and incorporates a fabric which has both a light transmission property and a light reflection property when the fabric is illuminated with light having wavelength(s) in the range of from about 400 nanometers to about 2200 nanometers, and particularly in the ranges from about 400 to about 800 nanometers and from about 700 to about 2200 nanometers.

The amount of light transmitted through the fabric relative to the amount of light reflected by the fabric is able to change when the fabric stretches in response to motion in the wearer's body due to changes in the flow of blood through an artery disposed beneath the fabric.

A radiation source that emits radiation with wavelength(s) in the range from about 400 nanometers to about 2200 nanometers, and particularly in the ranges from about 400 to about 800 nanometers and from about 700 to about 2200 nanometers, and a radiation detector are attached to the fabric in relative positions such that the reception of incident radiation by the detector is directly affected by a change in the amount of light transmitted through the fabric relative to the amount of light reflected by the fabric as the fabric stretches in response to motion in the body of a wearer due to changes in the flow of blood through an artery disposed beneath the patch occurring in consonance with variations in the air pressure within the inflatable cuff. A pressure recorder responsive to the signal output from the detector records the pressure of the cuff when the output of the detector is at a minimum value and the pressure in the cuff following the minimum when the signal from the detector again lies within a predetermined range of a baseline signal value. In one embodiment, the fabric forms a patch that is disposed on or over the inflatable arm cuff.

BRIEF DESCRIPTION OF THE DRAWINGS

The invention will be more fully understood from the following detailed description, taken in connection with the accompanying drawings, which form a part of this application, and in which.

DETAILED DESCRIPTION OF THE INVENTION

Figure 1:
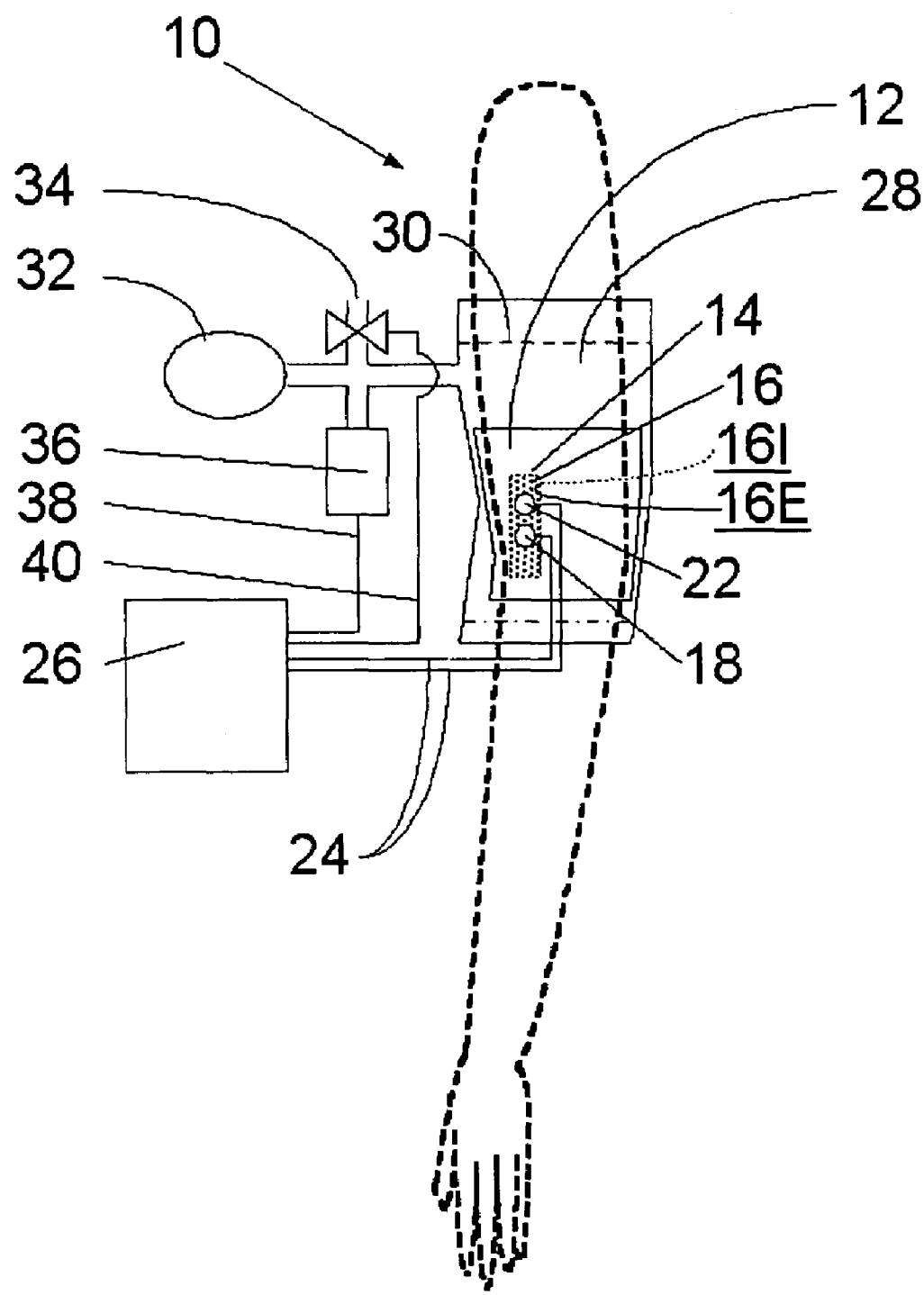
FIG. 1 is a schematic diagram of a system useful for the monitoring blood pressure of a subject by sensing geometric changes in the body of the subject due to the motion of blood passing through blood vessels underlying a patch of monitoring fabric.

Throughout the following detailed description similar reference characters refer to similar elements in all figures of the drawings.

FIG. 1 is a stylized pictorial representation of a system 10 useful with the method of the present invention for directly monitoring blood pressure of a subject by sensing motion due to geometric changes in the body of the subject associated with the flexing of arterial walls produced by blood pressure pulses.

As seen in FIG. 1, the system 10 includes a sleeve 12 having any convenient fabric construction (e.g., knitting, weaving) and made from any suitable textile filament apparel denier yarn. The sleeve 12 includes at least a portion, or patch, 14 formed from a monitoring fabric 16. The monitoring fabric 16 has an inner surface 16I and exterior or outer surface 16E. Although the patch 14 is represented as rectangular in shape in FIG. 1, it should be understood that the patch 14 may take any convenient or desired shape. If desired, a portion or even the entirety of the sleeve 12 may be made from the monitoring fabric 16.

The monitoring fabric 16 in accordance with the present invention exhibits both a light transmission property and a light reflection property when the fabric is illuminated with light having a wavelength in the extended range from about 400 to about 2200 nanometers. This range is extended in the sense that it encompasses both near infrared light and visible broad spectrum white light.

As used herein the term "broad spectrum white light" means light having a wavelength in the range from about four hundred (400) nanometers to about eight hundred (800) nanometers.

As used herein the term "near infrared light" means light having a wavelength in the range from about seven hundred (700) nanometers to about twenty two hundred (2200) nanometers. The wavelength of 805 nanometers or the wavelength of 880 nanometers may be used in systems operating in the near infrared spectrum. The wavelength of 805 nanometers is preferred.

In accordance with the present invention, the amount of light transmitted through the fabric 16 relative to the amount of light reflected by the fabric 16 is able to change as the fabric stretches. The fabric stretches in response to geometric changes of the body of the subject due to the flexing of the arteries in response to blood pressure pulses. The term "light balance" may be used herein to refer to the amount of light transmitted through the fabric 16 relative to the amount of light reflected by the fabric 16.

Light reflected by the fabric toward an aperture of acceptance defined with respect to an axis extending from the surface of the fabric is useful in producing a signal output from a detector located in the aperture. Alternatively, light transmitted through the fabric is "lost" to a detector placed at the aperture of acceptance.

The monitoring fabric 16 used in the patch 14 can be made from a reflective yarns, stretchable yarns any combination of reflective and stretchable yarn or any like material. In one exemplary construction a first plurality of reflective yarns is combined with a second plurality of stretchable yarns. The yarns can be combined in any conventional manner including woven or non-woven construction.

For woven constructions, yarns can be combined in plain weave, satin weave, twill weave or any other well known constructions. Woven fabrics may also include weft elastic, warp elastic or bielastic woven fabrics for varying fabric elasticity.

For non-woven constructions such as knit constructions, yarns can be combined by circular knit, warp knit or any other suitable knit construction. In circular knits, typical constructions are single jersey (i.e. different structure in front and back, e.g. 1×1 knit) and double jersey (i.e. same structure in front and back, e.g. 2×1 knit). The stitch size and distance determine the openness of the knit fabric. Warp knits may include tricot and raschel constructions where the tightness is determined by the number of needles/inch or the stitch size.

Any suitable apparel denier and any suitable needle combination or warp/weft intensity may be used in making the monitoring fabric. Each reflective yarn may comprise a coating of a specularly reflective material thereon. The coating may also be electrically conductive. Furthermore, the reflective yarn may be elastic. Each stretchable yarn is formed as a combination of an elastic yarn component and a hard yarn component.

In the preferred instance, the reflective yarn is that yarn sold by Laird Sauquoit Technologies, Inc. (300 Palm Street, Scranton, Pa., 18505) under the trademark X-STATIC® yarn. X-STATIC® yarn is based upon a 70 denier (77 dtex), 34 filament textured nylon available from INVISTA North America S. àr. l., Wilmington, Del. 19802, as product ID 70-XS-34X2 TEX 5Z electroplated with electrically conductive silver.

Alternatively, another method of forming the monitoring fabric 16 is to screen-print a pattern using an electrically conductive ink after constructing the yarns in any conventional woven or non-woven manner. Suitable electrically conductive inks include, but are not limited to, those sold by DuPont Microcircuit Materials, Research Triangle Park, N.C. 27709, as silver ink 5021 or silver ink 5096, and the like.

A screen-printed pattern of conductive inks must also allow the fabric to move. Preferably, the conductive ink does not affect the ability of the fabric to stretch and recover. One way to prevent affecting the stretch and recovery properties of fabric is to screen-print a pattern of conductive ink(s) in the form of a matrix of dots. Such a dot matrix pattern provides full freedom of movement for the yarns in the fabric, while still exhibiting desired light reflection and transmission properties.

The patch 14 of monitoring fabric 16 can alternatively be formed from elastic and electrically conductive composite yarn comprising a core yarn made of, for instance, LYCRA® spandex yarn wrapped with insulated silver-copper metal wire obtained from ELEKTRO-FEINDRAHT AG, Escholzmatt, Switzerland, using a standard spandex covering process. The core yarn may further be covered with any nylon hard yarn or polyester hard yarn.

Stretchable yarn can be formed in any conventional manner. For example, the stretchable yarn can be formed as a combination of a covered elastic yarn and a hard yarn.

In one preferred embodiment, the covered elastic yarn can be comprised of a twenty (20) denier (22 dtex) LYCRA® spandex yarn single-covered with a ten (10) denier (11 dtex) seven filament nylon yarn. LYCRA® spandex yarn is available from INVISTA North America S. á r. l., Wilmington, Del. 19805. Alternatively, the elastic yarn component of the present invention may comprise elastane yarn or polyester bicomponent yarns, such as those known as ELASTERELL-P™ from INVISTA North America S. á r. l., Wilmington, Del. 19805. The terms spandex and elastane are used interchangeably in the art. An example of a branded spandex yarn suitable for use with the present invention is LYCRA®.

Synthetic bicomponent multifilament textile yarns may also be used to form the elastic yarn component. One preferred synthetic bicomponent filament component polymer can be thermoplastic. The synthetic bicomponent filaments can be melt spun or formed in any other manner common in the art of filament formation. In the most preferred embodiment, the component polymers can be polyamides or polyesters.

A preferred class of polyamide biocomponent multifilament textile yarns comprises those nylon biocomponent yarns which are self-crimping, also called "self-texturing". These bicomponent yarns comprise a component of nylon 66 polymer or copolyamide having a first relative viscosity and a component of nylon 66 polymer or copolyamide having a second relative viscosity, wherein both components of polymer or copolyamide are in side-by-side relationship as viewed in the cross section of the individual filament. Self-crimping nylon yarn such as that yarn sold by INVISTA North America S. àr. l, Wilmington, Del, 19805 under the trademark TACTEL® T-800™ is an especially useful bicomponent elastic yarn.

Some examples of polyester component polymers include polyethylene terephthalate (PET), polytrimethylene terephthalate (PTT) and polytetrabutylene terephthalate. In one preferred embodiment, polyester bicomponent filaments comprise a component of PET polymer and a component of PTT polymer in a side-by-side relationship as viewed in the cross section of the individual filament. One exemplary yarn having this structure is sold by INVISTA North America S. á r. l., Wilmington, Del. 19805 under the trademark T-400™ Next Generation Fiber.

The hard component could be made from any inelastic synthetic polymer fiber(s) or from natural textile fibers, such as wool, cotton, ramie, linen, rayon, silk, and the like. The synthetic polymer fibers may be continuous filament or staple yarns selected from the multifilament flat yarns, partially oriented yarns, textured yarns, bicomponent yarns selected from nylon, polyester or filament yarn blends. The hard component is preferably 260 denier (286 dtex) 68 filament nylon yarn.

Nylon yarns may comprise synthetic polyamide component polymers, such as nylon 6, nylon 66, nylon 46, nylon 7, nylon 9, nylon 10, nylon 11, nylon 610, nylon 612, nylon 12 and mixtures and copolyamides thereof. In the case of copolyamides, especially preferred are those including nylon 66 with up to 40 mole percent of a polyadipamide wherein the aliphatic diamine component is selected from the group of diamines available from E.I. Du Pont de Nemours and Company of Wilmington, Del. under the respective trademarks DYTEK A® and DYTEK EP®.

Further in accordance with the present invention, the hard yarn portion may comprise polyesters such as, for example, polyethylene terephthalate (PET), polytrimethylene terephthalate (PTT), polybutylene terephthalate and copolyesters thereof.

The monitoring fabric 16 may also be formed from composite yarns in which the reflective and stretchable components are combined in the same yarn. Such a composite yarn would include a covering yarn having a spectrally reflective outer surface that is wrapped about an elastic yarn component in one or more layers.

The remainder of the structure of the sleeve 12, if not also formed of the monitoring fabric, may exhibit any convenient textile construction (e.g. knitting or weaving as described above), and may be made from any suitable textile filament apparel denier yarn.

In one embodiment, the monitoring fabric 16 used in the patch 14 is attached to the sleeve 12. The patch 14 could be sewn, glued, taped, buttoned, interwoven or attached to the sleeve by any conventional means. In another embodiment, the sleeve 12 is completely constructed of the monitoring fabric 16.

The present invention is directed to monitoring the light balance of a monitoring fabric 16 as it stretches and recovers. For this purpose, the system 10 includes a suitable source 18 of radiation operable in the wavelength range from about 400 nanometers to about 2200 nanometers, and particularly in the ranges from about 400 to about 800 nanometers and from about 700 to about 2200 nanometers. An associated detector 22 is responsive to incident radiation in the given wavelength range and subranges for producing signals in response thereto.

In the case of operation with near infrared light, the radiation source 18 can be a compound semiconductor-based (e.g., gallium arsenide or gallium aluminum arsenide) photo-emitting diode operating in the infrared range (at a wavelength of, for example, 805 nanometers or 880 nanometers). The detector 22 can be any device that can detect radiation, for instance, a photodiode coupled to appropriately configured output amplification stages. Any well known semiconductors can be used for forming the photodiode including silicon or germanium. A commercially available radiation source and detector package suitable for use in the system of the present invention is that available from Fourier Systems Ltd. (9635 Huntcliff Trace, Atlanta, Ga., 30350) as model DT155 (0-5 volt output).

For broad spectrum white light (400 to 800 nanometers) operation, the source 18 can be a compound semiconductor-based "white LED" (e.g., a light emitting diode employing an indium gallium nitride based device with suitable phosphors to provide broad spectrum white light emission). An LED source of broad spectrum white light is available from Lumitex® Inc., 8443 Dow Circle, Strongsville, Ohio 44136, USA; Part No. 003387. Such an LED provides radiation in the wavelength range of 430 to 700 nanometers. The detector 22 is a preferably a silicon phototransistor coupled to appropriately configured output amplification stages.

The radiation source 18 and the detector 22 are attached to monitoring fabric 16 in predetermined relative positions. The positions were determined such that the reception of incident radiation by the detector 22 is directly affected by a change in the amount of light transmitted through the monitoring fabric 16 relative to the amount of light reflected by the monitoring fabric 16 when the fabric stretches and recovers. In the preferred case, the radiation source 18 and detector 22 are embedded, or fixed firmly, into the textile structure of the monitoring fabric 16. The radiation source 18 and detector 22 can be fixed using any well known attachment method, including, but not limited to, clamping, gluing, sewing, taping, or hook and loop fasteners (Velcro). Optionally, it may be desirable in some operational configurations of the invention to dispose both the source and the detector remotely from and not in direct contact with the fabric 16. In such a remote arrangement, the radiation source 18 and detector 22 could be located in any arrangement that permits the detector 22 to detect changes in the transmission and reflection of radiation during stretching and recovery.

The source 18 may be arranged in such a way as to maintain its relative position to the detector 22. For instance, the source 18 and the detector 22 may be rigidly connected together on one side of the fabric 16 to maintain a spatial relationship. Alternatively, the position of the source 18 relative to the detector 22 can be maintained on opposite sides of the monitoring fabric 16 for monitoring light transmission. In such an embodiment, the radiation source is connected to the radiation detector using a "clothes-pin" or alligator style clamp. Other well known means of maintaining spatial relationship between the source and the detector are contemplated.

The apparatus 10 represented in FIG. 1 further includes an inflatable cuff 28 substantially similar to a standard cuff known in the blood pressure measurement art. The cuff 28 is typically a woven nylon sleeve with a seamless inner bladder 30 of latex rubber. The inner bladder 30 communicates with an external air pump 32, valve 34 and a pressure measurement device 36 for measuring the internal pressure of the bladder 30. The pressure measurement device 36 communicates electrically with the processor 26 over an electrical connection 38. The valve 34 may be configured for automatic operation by the signal processor 26 over a control line 40.

The pump 32 may take the form of any conventional pump including a manually operated device, an automated piston or diaphragm air pump. The pressure measurement device 36 may be implemented using a manometer of known design. Such a manometer is constructed using known barometric measurement techniques that include a column of mercury, a Bourdon gauge movement, and a measurement device having a high reproducibility of measurement in the expected range of operation, for example, from about ten (10) millimeters of mercury to about five hundred (500) millimeters of mercury (mm Hg). A suitable pressure measurement device 36 could be a direct capacitance measurement device provided with a fully electronic output suitable for use with traditional digital signal processors. A pressure transducer operable to measure the pressure within the cuff at predetermined sampling time intervals is also suitable for use as the pressure measurement device. The miniature silicon pressure sensor package available from Advanced Custom Sensors, Inc. Irvine, Calif., 92618 as Model 7277 (zero to five volt output; zero to seven pounds per square inch gage rating) is such a device, though any similar means for measuring pressure is contemplated.

The principles of operation by which the motion of a subject's body due to geometric changes generated by blood pressure pulses may be monitored in accordance with the system of the present invention may be more clearly understood with reference to FIGS. 2A through 2F. In the discussion that follows both the source 18 and the detector 22 are mounted adjacent to the same surface 16E of the monitoring fabric 16 so as to operate in a "reflection mode". Alternatively, it is contemplated within the scope of the invention to operate in a "transmission mode". In the alternative transmission mode of operation, the source 18 and the detector 22 are mounted to opposite sides of the monitoring fabric 16.

Figure 2A:
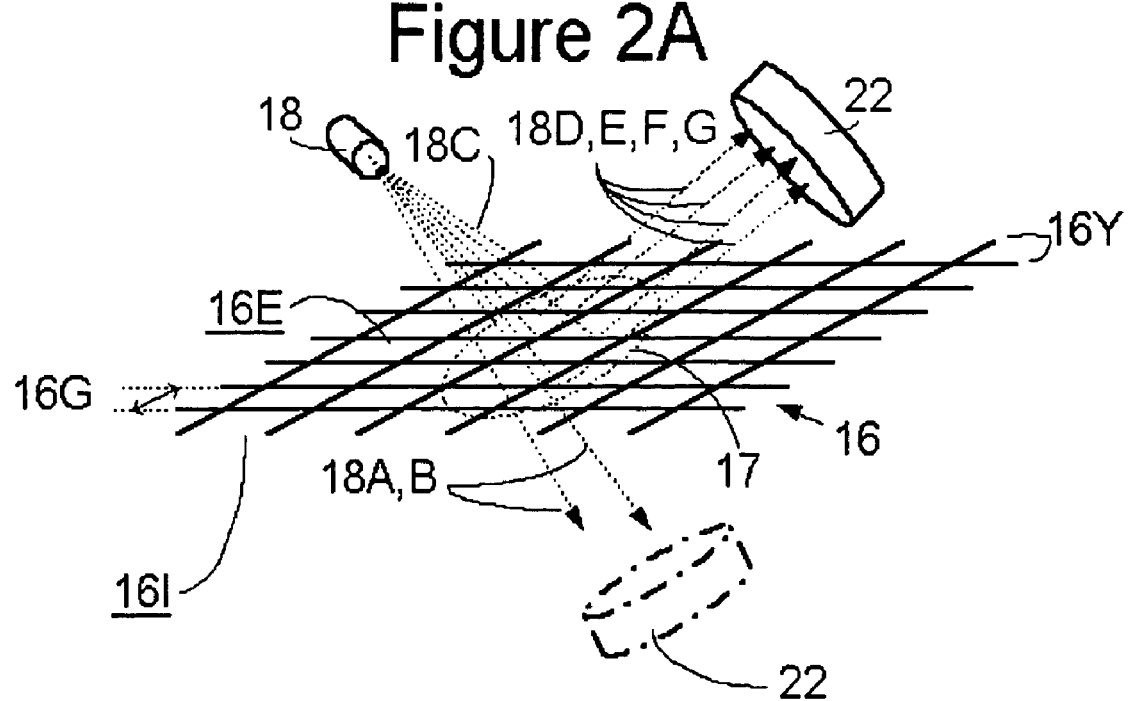
FIGS. 2A and 2B are diagrammatic views illustrating possible light transmission and reflection response of the fabric used in the monitoring system of the present invention during normal systole and diastole phases of heart action.
Figure 2B:
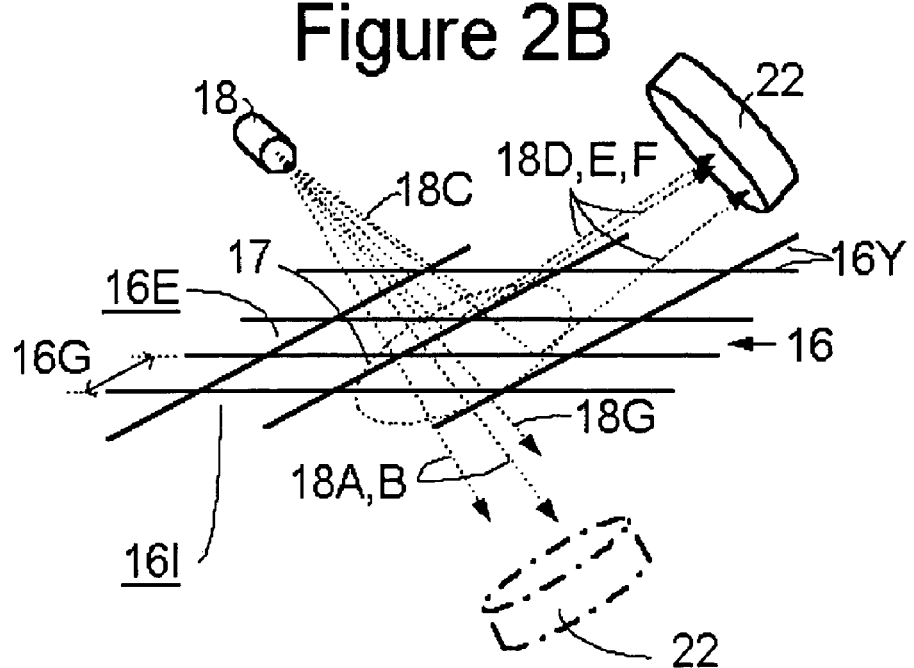

The reaction of the fabric 16 during normal diastole and systole phases of heart action are depicted in FIGS. 2A and 2B.

As represented in FIG. 2A in a normal diastole phase the yarns 16Y forming the monitoring fabric 16 lie within a relatively close distance of each other to define a pattern of relatively narrow gaps 16G. A generally circular spot indicated by the reference character 17 represents the area of the monitoring fabric 16 illuminated by the source 18. Of the photons emitted from the radiation source 18 toward the surface 16E of the fabric 16 some photons are absorbed (e.g., represented by a ray 18C) by the yarns 16Y of the fabric while other photons (e.g., the rays 18A and 18B) pass through gaps 16G therein. These photons are lost to the detector 22. The major portion of the light (e.g., represented by the rays 18D through 18G) is reflected from the surface 16E of the monitoring fabric 16 toward the detector 22. This major portion of the light is detected by detector 22, which in turn produces a corresponding output signal.

During a normal systole phase of a heart beat, the size of the gaps 16G formed in the monitoring fabric 16 increases in response to motion induced by the flexure of the underlying blood vessels. This increase in size of the gaps 16G (FIG. 2B) increases the likelihood that a photon will pass through the fabric 16, and decreases the likelihood that a photon will reflect toward the detector 22. The total number of photons lost to the detector 22 by transmission through or absorption by the fabric (e.g., represented by the rays 18A, 18B and 18C) increases. The signal output from the detector 22 concomitantly decreases. Although the number of photons lost to the detector 22 by absorption (e.g., represented by the ray 18C) does not necessarily change, the likelihood that a photon will strike a yarn 16F and be reflected or absorbed decreases since the spot size 17 remains constant in the area while the gap 16G size increases.

As the systolic phase of the pulse beat gives way to the diastolic phase, the fabric 16 undergoes the elastic recovery. The gaps 16G return to their original size (FIG. 2A). The major portion of the light is again reflected toward the detector 22, increasing the output signal therefrom.

Figure 2C:
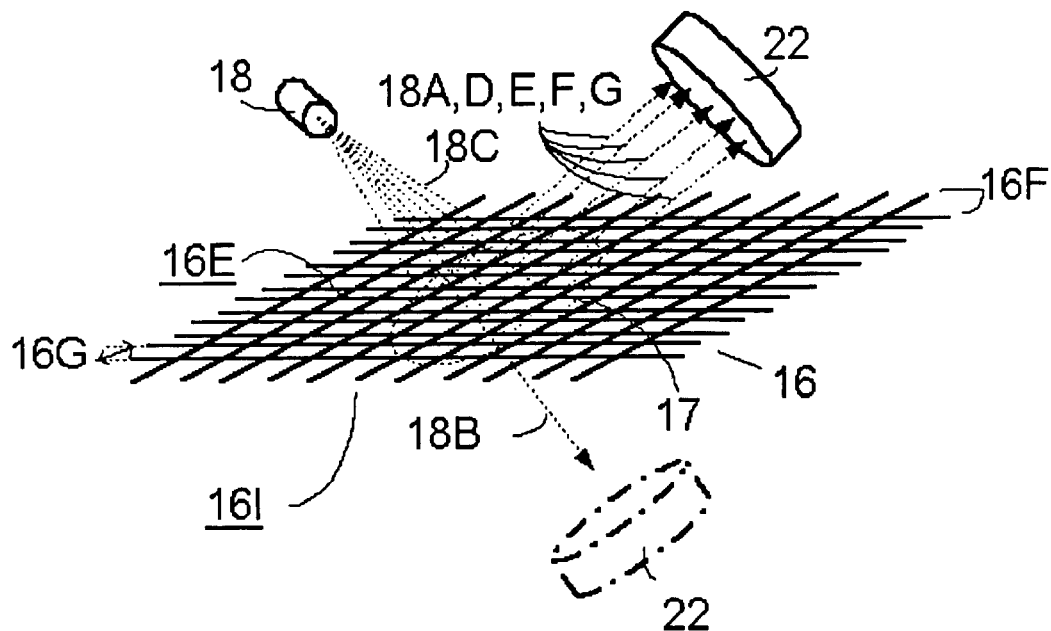
FIGS. 2C and 2D are respective diagrammatic views illustrating possible light transmission and reflection response of the fabric when a blood vessel underlying a patch formed of such fabric is totally occluded and when blood flow is re-established.
Figure 2D:
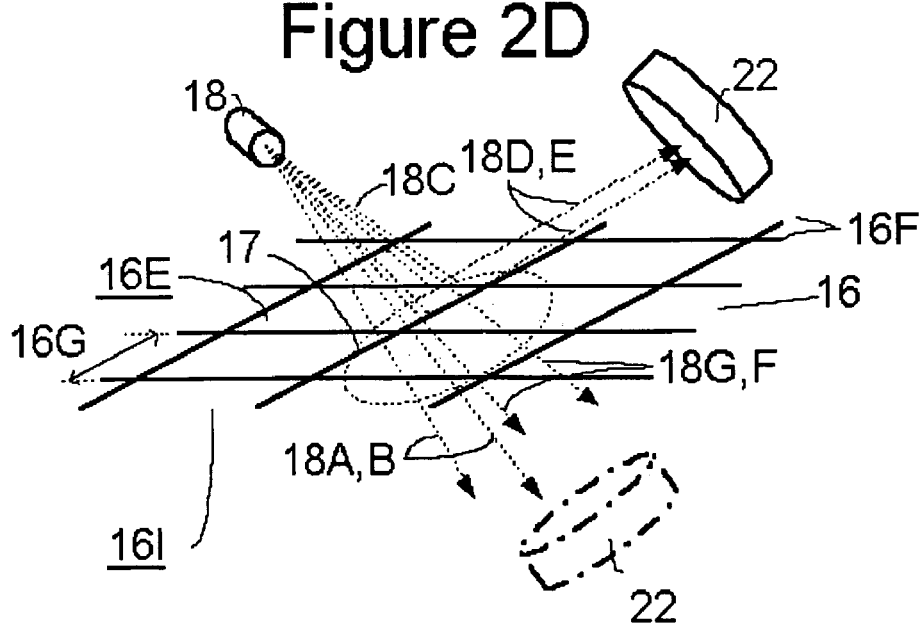
Figure 2E:
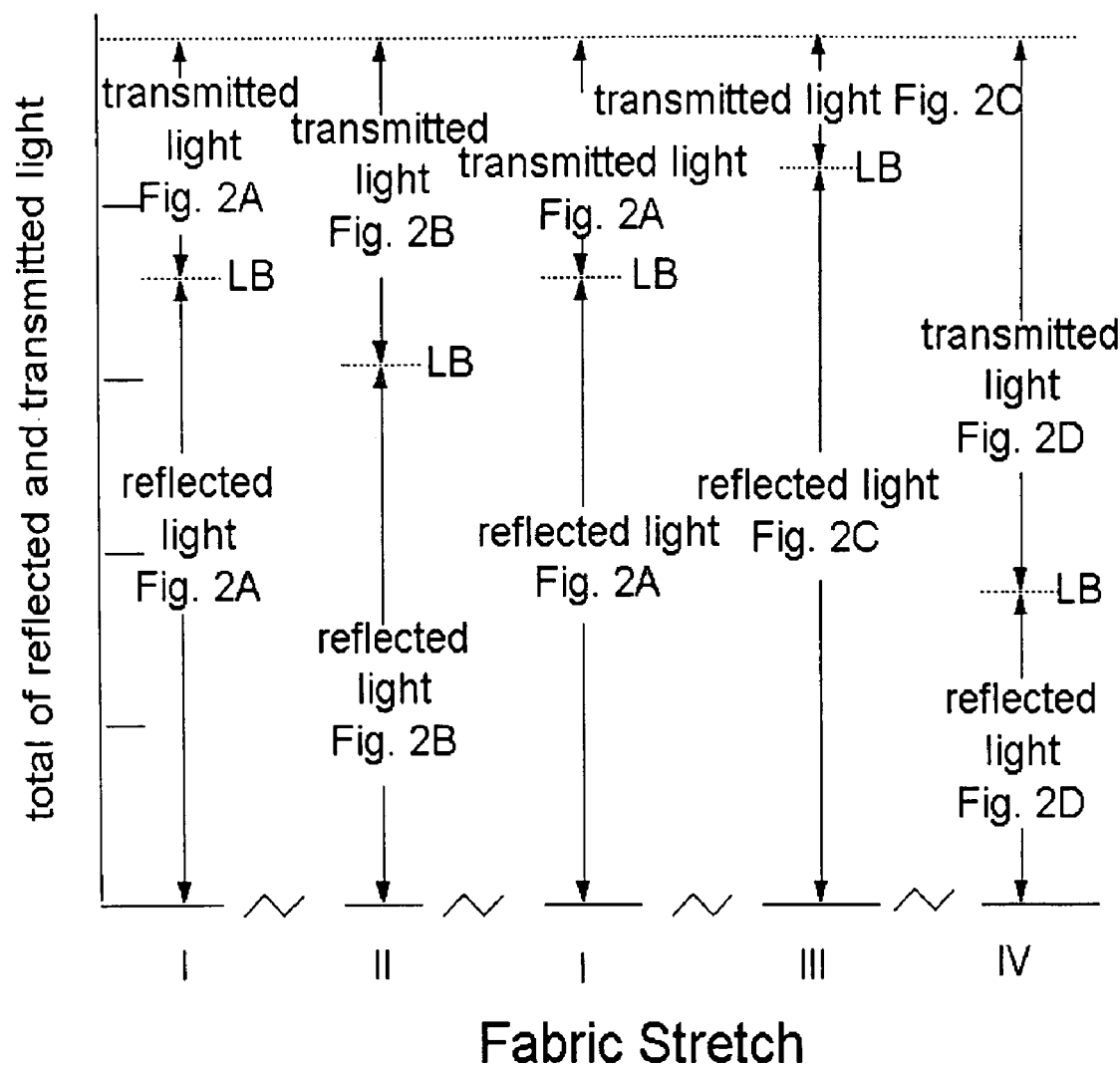
FIG. 2E is a graphical representation of the change in the amount of light transmitted through the fabric relative to the amount of light reflected by the fabric as the fabric stretches and recovers during normal systole and diastole phases of heart action (FIGS. 2A and 2B), and when a blood vessel underlying the fabric is totally occluded and when blood flow is thereafter re-established (FIGS. 2C and 2D)

The left hand portion of FIG. 2E illustrates the waveform of the signal generated at the detector 22 as the fabric undergoes its stretch cycle from the initial diastolic phase (represented by the reference character "I") through a systolic phase (represented by the reference character "II") and back to the diastolic phase ("I"). This portion of FIG. 2E graphically illustrates that during the course of a stretch cycle the light balance (reference character "LB" in FIG. 2E) of the fabric changes.

As shown in FIG. 2E, at diastolic phase ("I") of FIG. 2A, the reflected light represented by the bottom portion below the "LB" is greater than the transmitted light represented by the upper portion above the "LB". In contrast, FIG. 2E shows that at systolic phase ("II") of FIG. 2B, the reflected light represented by the bottom portion below the "LB" is less than the transmitted light represented by the upper portion above the "LB".

Comparison between the diastolic and systolic phases indicates that the amount of light transmitted through the monitoring fabric 16 relative to the amount of light reflected by the monitoring fabric 16 changes in a periodic fashion over time as the fabric stretches. Light lost to the detector 22 by absorption may be considered as contributing to the "transmitted light" section of the graph of FIG. 2E. This periodic variation in light balance is represented in the left-hand portion of FIG. 2F as a time-varying signal synchronized with the elongation and recovery stages of fabric stretch (e.g., diastolic phase represented by character "I" and systolic phase represented by character "II").

The situation that arises when a cuff is fully pressurized is depicted in FIG. 2C. In this case the flow of blood is completely interrupted and no flexure of the underlying artery occurs. The fabric 16 reverts to a fully unstretched condition with the gap spacing 16G between yarns 16Y being at its minimum. Substantially all of the photons falling on the illuminated spot 17 are reflected toward the detector 22 resulting in the light balance depicted at reference character "III" in the right hand portion of FIG. 2E. At reference "III", the reflected light represented by the bottom portion below the "LB" is significantly greater than the transmitted light represented by the upper portion above the "LB".

Figure 2F:
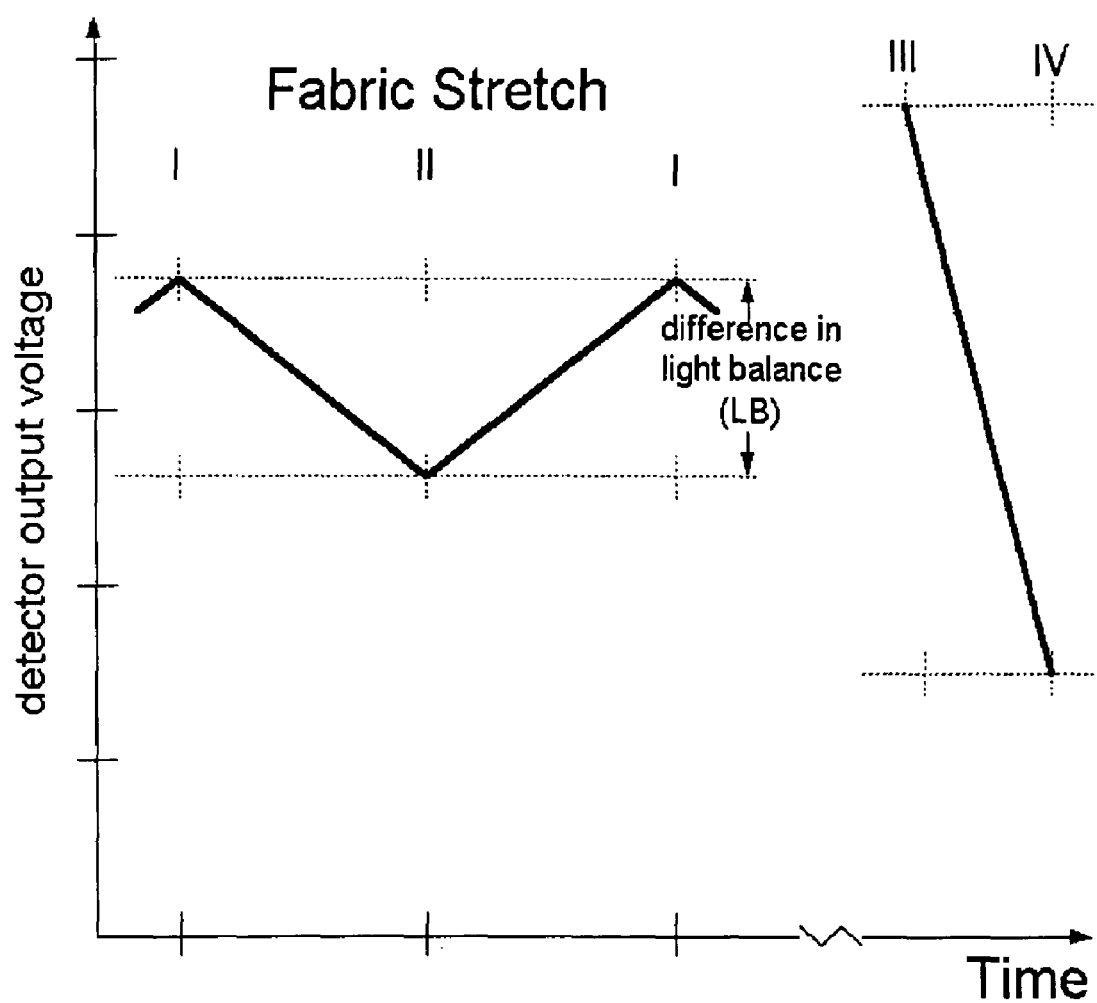
FIG. 2F is a graphical representation of a signal, periodic in time, representing the changes in the amount of light transmitted through the monitoring fabric relative to the amount of light reflected by the monitoring fabric as represented in FIG. 2E.

FIG. 2D depicts the situation when blood flow through the previously occluded artery is re-established. The sudden rush of blood through the artery elongates the fabric 16 and extends the gaps 16G to a wider extent than in the systolic phase (shown in FIG. 2B). The amount of light transmitted through the fabric 16 increases commensurately while the amount of light reflected significantly decreases. This result is illustrated in the change in light balance depicted at reference character "IV" in the right hand portion of FIG. 2E. In FIG. 2E, at reference character "IV", the reflected light represented by the bottom portion below the "LB" is less than the transmitted light represented by the upper portion above the "LB". The right hand portion of FIG. 2F illustrates the rapid decrease in signal output from the detector 22 caused by the sudden rush of blood through the previously occluded artery (e.g., the change in detector output voltage from phase "III" to phase "IV" shown in FIG. 2F)

As the rush of blood diminishes the light balance and the signal output from the detector 22 would revert toward the ranges exhibited during normal diastolic and systolic operation.

Operation

In an exemplary mode of operation the apparatus of the present invention would be applied to the arm of a person generally in the position indicated by the dotted outline in FIG. 1, with the fabric patch 14 of sleeve 12 over the brachial artery. The inflatable cuff 28 is applied over the sleeve 12.

Figure 3:
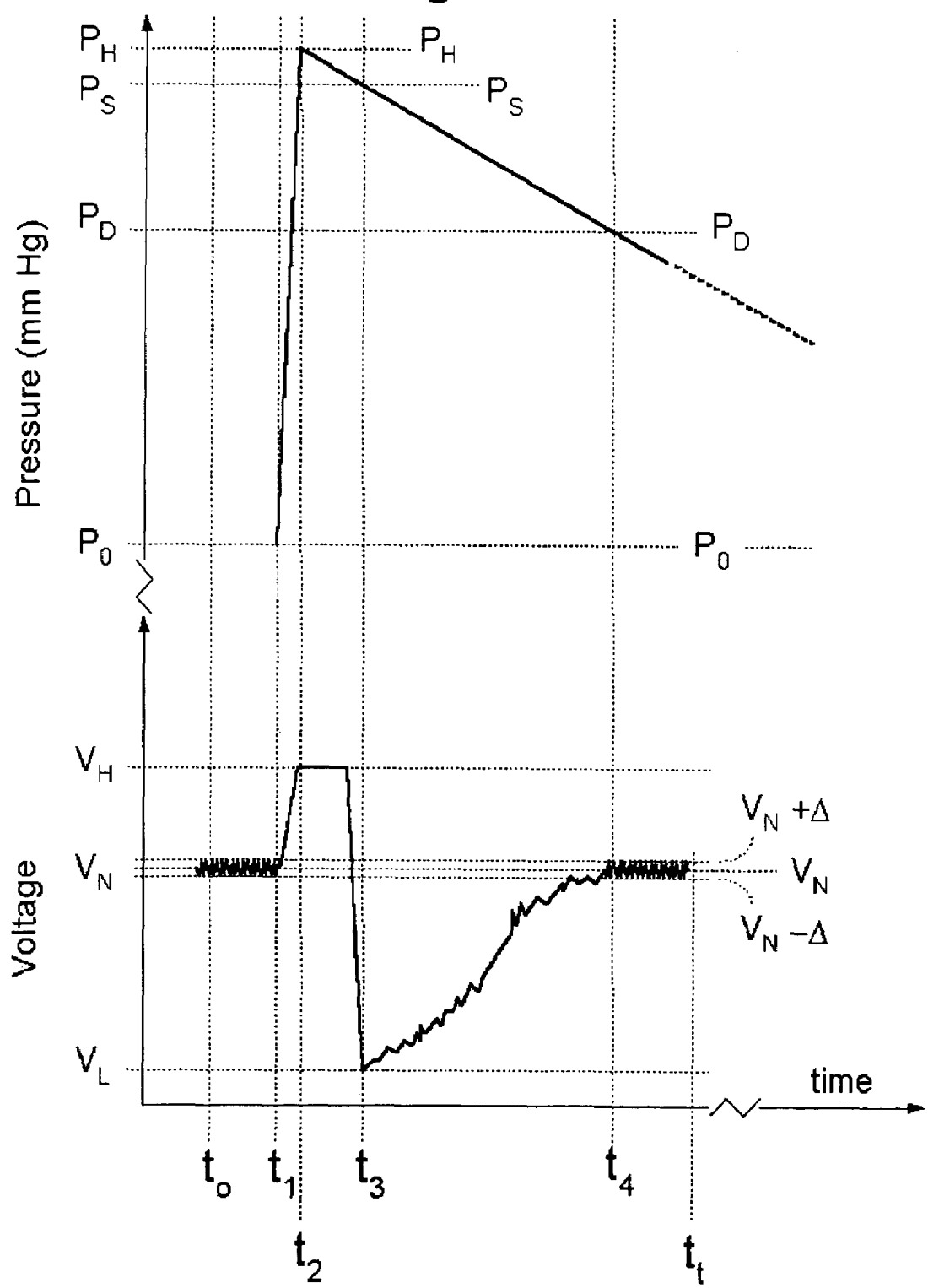
FIG. 3 is a diagram illustrating the temporal relationship between pressure measured in an inflatable cuff disposed over an artery of a wearer and the voltage appearing of the detector when the method and system of the present invention is used to monitor blood pressure of the wearer.

FIG. 3 illustrates the temporal relationship between pressure measured in the cuff 28 and a voltage resulting from the radiation detected by the detector 22 in reflection mode. In a reflection mode of operation, the source 18 and the detector 22 are arranged adjacent to side 16E of the fabric 16. As discussed in connection with FIGS. 2A through 2F, any fabric 16 elongation is accompanied by a decreasing signal (voltage) from the detector 22, corresponding to increased light transmission through the fabric 16.

Considering again FIG. 3, the pressure in the cuff 28 is at atmospheric pressure $P_0$ during the time interval between $t_0$ and $t_1$. Also, during this same time interval the signal at detector 22 is a mean value $V_N$ varying between the limits of ($V_N+\Delta$ and $V_N-\Delta$)

This mean voltage $V_N$ results from the subtle flexing of the arterial walls and subsequent subtle movement of tissue underlying the fabric 16. This subtle movement is due to the arterial pressure fluctuations from the systolic to the diastolic pressure extremes. Because blood flow is laminar and silent during this interval, the net average force on the arterial walls is constant. During the arbitrary time interval $t_0$ to $t_1$, the voltage reading from detector 22 is sampled; and a voltage $V_N$ (+/−$\Delta$) is stored in memory of the processor 26.

Next, at time $t_1$, under control of the processor 26, the valve 34 is closed and the pump 32 activated. Accordingly, during the time interval from $t_1$ to $t_2$, the pressure in the cuff 28 rises to a pressure $P_H$, a pressure value chosen to be above the highest expected systolic pressure (e.g. 300 to 330 mm Hg). This pressure value is also stored in memory of the processor 26. During this time interval, the brachial arterial blood flow becomes totally interrupted. Effectively, there is no arterial wall flexing or underlying body tissue movement because blood flow is occluded. As explained in connection with FIG. 2C, the voltage output from the detector 22 rises to $V_H$.

During the time interval from $t_1$ to $t_2$, the cuff pressure and detector voltage are sampled and stored at a fixed sampling frequency (chosen in a frequency range from ten (10) Hertz to ten thousand (10,000) Hertz). The voltage reading from detector 22 when the pressure in cuff 28 reaches its maximum value $P_H$ (at time $t_2$ in FIG. 3) is stored in processor 26.

At $t_2$ the pressure in the cuff 28 is released by opening valve 34 under control of the processor 26. During the time interval $t_2$ to $t_3$ the voltage output from detector 22 and the pressure in the cuff 28 are sampled and stored at the sampling frequency. During the interval $t_2$ to $t_3$ the rate of pressure change within the cuff 28 is about two (2) mm Hg to about six (6) mm Hg per second.

As the cuff pressure is reduced, at some time within the interval $t_2$ to $t_3$ the pressure in the cuff 28 is equal to the systolic (highest) arterial blood pressure and the artery snaps open with a sudden flow of blood. In turn, as explained in connection with FIG. 2D, the voltage at the detector 22 experiences a maximum in rate of change and falls to a maximum deviation from $V_N$, to a voltage value $V_L$. As shown in FIG. 3, this voltage $V_L$, detected at $t_3$, corresponds to the sudden rush of arterial blood filing the formerly occluded artery with a sharp flexing of the artery walls. This sharp flexing of the walls in turn stimulates movement of the tissue overlying the artery and underlying the fabric 16. This movement corresponds to a maximum amplitude for the motion of the tissue underlying the fabric 16. At $t_3$, corresponding to voltage $V_L$, this maximum amplitude in tissue movement forces maximum fabric 16 flexing, sudden elongation, signaling that a peak or systolic pressure $P_S$ is present in the brachial artery.

During the interval of time $t_3$ to $t_4$ the pressure in the cuff 28 is further decreasing. The voltage and pressure values are sampled at the predetermined frequency. The voltage output at the detector 22 continues to rise during this time interval $t_3$ to $t_4$.

Following the occurrence of the minimum voltage $V_L$, the output voltage of the detector again returns to within the predetermined range about the baseline value (within the limits ($V_N+\Delta$ and $V_N-\Delta$) and the pressure in the cuff 20 passes through a point of equivalence with the diastolic (lowest) pressure in the brachial artery, uniquely defining $t_4$. Any further drop in pressure in the cuff 28, to atmospheric pressure, produces no further rise in voltage at detector 22 during the time interval $t_4$ to $t_t$.

The system and method of the present invention may alternatively be operated in a transmission mode where the source 18 is disposed on side 16E of the fabric 16 while the detector 22 is disposed on the opposite side 16I. The dot-dashed outline of detector 22, shown in FIGS. 2A through 2D represents the location of detector 22 in transmission mode. The light balance between reflection and transmission will be the same as the situation discussed in connection with the reflection mode. However, the detector output voltage shown in FIG. 2F is reversed since more fabric stretch results in higher light transmission providing a commensurately higher detector voltage. The detector voltage waveform shown in FIG. 3 is therefore reversed or inverted as well. In contrast to the reflection mode shown in FIG. 3, the transmission mode measures a decrease in voltage between the interval of time $t_1$ to $t_2$ and an increase between the interval of time $t_2$ to $t_3$. Finally, in contrast to FIG. 3 the detector voltage decreases between $t_3$ and $t_4$ to return to voltage $V_N$.

The measurement of pressures $P_S$ and $P_D$ is, in principle, determined by means of signal processing techniques known in the art. For example, one commercially available pressure transducer 36, Model 7277 from Advanced Custom Sensors, Inc. Irvine, Calif., 92618, is a miniature silicon pressure sensor package, with 0 to 5 volt output, and 0 to 7 pound per square inch gage rating. This pressure transducer 36 will communicate directly with signal processor 26 such as a Z8® microcontroller, Model Z86C08 from ZILOG, Inc., Campbell, Calif., 95008-6600 with electronically programmable memory and associated circuitry.

Those skilled in the art, having the benefit of the teachings of the present invention as hereinabove set forth, may effect modifications thereto. Such modifications are to be construed as lying within the scope of the present invention, as defined by the appended claims.

What is claimed is:

1. A system for monitoring blood pressure comprising:
   an inflatable arm cuff that is selectably inflatable to differing air pressures;
   a patch disposed in or on said arm cuff comprising fabric that has both a light transmission property and a light reflection property that change when the fabric stretches;
   a radiation source mounted to the fabric, wherein said radiation source directs radiation onto the fabric; and
   a radiation detector mounted to the fabric.

2. The system of claim 1, wherein
   the radiation source emits radiation with a wavelength in the range of from about 400 to about 2200 nanometers; and
   the detector responds to incident radiation with a wavelength in the range of from about 400 to about 2200 nanometers.

3. The system of claim 1, wherein the source and detector are attached to the fabric in relative positions such that the reception of incident radiation by the detector is directly affected by a change in the amount of light transmitted though the fabric relative to the amount of light reflected by the fabric as the fabric stretches in response to motion in the body of a wearer due to changes in the flow of blood through an artery disposed beneath the patch occurring in consonance with variations in the air pressure within the inflatable cuff.

4. The system of claim 1, wherein the fabric is integral with the cuff.

5. The system of claim 1 wherein the fabric comprises a first plurality of reflective yarns woven or knit with a second plurality of stretchable yarns.

6. The system of claim 1 wherein
   the fabric has a first and a second side; and wherein
   the source and the detector are mounted on a same side of the fabric.

7. The system of claim 1 wherein
   the fabric has a first and a second side; and wherein
   the source and the detector are mounted on opposing sides of the fabric.

8. A system for monitoring blood pressure of a wearer, the system being usable with an inflatable arm cuff, the arm cuff being sized for receipt over a portion of the body of a wearer, the cuff being selectably inflatable to differing air pressures to modify the flow of blood through an artery located in the portion of the body of a wearer over which the cuff is disposed, the blood pressure monitoring system comprising:
   a patch at least a portion of which is formed from a fabric which has both a light transmission property and a light reflection property when the fabric is illuminated with light and in which the amount of light transmitted through the fabric relative to the amount of light reflected by the fabric is able to change when the fabric stretches in response to geometric changes in the body of a wearer due to changes in the flow of blood through an artery disposed beneath the patch;
   a source of radiation with a wavelength in the range from about 400 to about 2200 nanometers;
   a detector that produces a signal in response to incident radiation with a wavelength in the range from about 400 to about 2200 nanometers;
   the source and detector being attached to the fabric in relative positions such that the reception of incident radiation by the detector is directly affected by a change in the amount of light transmitted through the fabric relative to the amount of light reflected by the fabric as the fabric stretches in response to motion in the body of a wearer due to changes in the flow of blood through an artery disposed beneath the patch occurring in consonance with variations in the air pressure within the inflatable cuff; and a pressure recorder responsive to the signal output from the detector for recording the pressure of the cuff when the output of the detector is at a minimum value, and for recording the pressure in the cuff following the minimum value when the signal from the detector again lies within a predetermined range of a baseline signal value.

9. The monitoring system of claim 8, wherein the fabric has a first and a second side; and wherein the source and the detector are mounted on opposing sides of the fabric.

10. The monitoring system of claim 8 wherein the fabric has a first side and a second side; and wherein the source and the detector are mounted on the same side of the fabric.

* * * * *